United States Patent
Cooley et al.

(10) Patent No.: US 7,700,133 B2
(45) Date of Patent: Apr. 20, 2010

(54) ANTIMICROBIAL FORMULATIONS AND METHODS OF USING THE SAME

(76) Inventors: Marianna Cooley, 8550 Westland West Blvd., Houston, TX (US) 77041; Timothy W. Fraser, 105 Mt. Rose St., Reno, NV (US) 89509

( * ) Notice: Subject to any disclaimer, the term of this patent is extended or adjusted under 35 U.S.C. 154(b) by 214 days.

(21) Appl. No.: 10/597,486

(22) PCT Filed: Feb. 17, 2005

(86) PCT No.: PCT/US2005/005190

§ 371 (c)(1),
(2), (4) Date: Aug. 11, 2008

(87) PCT Pub. No.: WO2005/079738

PCT Pub. Date: Sep. 1, 2005

(65) Prior Publication Data

US 2008/0286212 A1    Nov. 20, 2008

Related U.S. Application Data

(60) Provisional application No. 60/542,636, filed on Feb. 18, 2004.

(51) Int. Cl.
| | | |
|---|---|---|
| *A61K 33/00* | (2006.01) | |
| *A61P 31/00* | (2006.01) | |
| *A61Q 11/00* | (2006.01) | |
| *A61K 6/00* | (2006.01) | |
| *A61K 33/24* | (2006.01) | |
| *A61K 33/08* | (2006.01) | |
| *A61K 33/16* | (2006.01) | |
| *A61K 33/22* | (2006.01) | |
| *A61K 33/26* | (2006.01) | |
| *A61K 33/30* | (2006.01) | |
| *A61K 33/34* | (2006.01) | |
| *A61K 33/38* | (2006.01) | |
| *A61K 33/42* | (2006.01) | |

(52) U.S. Cl. .......................... 424/600; 424/49; 424/52; 424/57; 424/601; 424/604; 424/617; 424/618; 424/630; 424/635; 424/641; 424/647; 424/653; 424/659; 424/679; 424/688

(58) Field of Classification Search ........................ None
See application file for complete search history.

(56) References Cited

U.S. PATENT DOCUMENTS

| | | | | |
|---|---|---|---|---|
| 3,926,646 | A | * | 12/1975 | Inoue ........................... 106/35 |
| 4,849,223 | A | | 7/1989 | Pratt et al. |
| 5,009,898 | A | | 4/1991 | Sakuma et al. |
| 5,037,634 | A | | 8/1991 | Williams et al. |
| 5,213,615 | A | | 5/1993 | Michl |
| 5,413,788 | A | | 5/1995 | Edwards et al. |
| 5,468,489 | A | | 11/1995 | Sakuma et al. |
| 5,595,750 | A | | 1/1997 | Jacobson et al. |
| 6,017,553 | A | | 1/2000 | Burrell et al. |
| 6,106,854 | A | * | 8/2000 | Belfer et al. ................. 424/405 |
| 6,124,374 | A | | 9/2000 | Kolias et al. |
| 6,383,273 | B1 | * | 5/2002 | Kepner et al. ............ 106/15.05 |
| 2003/0170314 | A1 | * | 9/2003 | Burrell et al. ................ 424/618 |
| 2004/0002557 | A1 | | 1/2004 | Qian |
| 2004/0065225 | A1 | | 4/2004 | Ruebel et al. |

OTHER PUBLICATIONS

Richard Dunivant; "White Line Disease," "Onychomycosis," "Stall Rot," "Hollow Foot," "Wall Thrush," "Yeast Infection," "Seedy Toe"—What is it?; Jun. 2000, http://www.horseshoes.com/advice/whitelinedisease/dunivant2/dunivant2.htm; retrieved Mar. 24, 2009.*

Frazier, Timothy W., "The History of Red Copper Cement and Its Resurgance as an Unsurpassable Dental Material," American Dental Association Meeting, Oct. 2002, New Orleans, LA.

Dumas et al., "Bacteriocidal Effects of Copper Cements", 27(2) Tufts Dental Outlook (1954), pp. 3-5.

Paffenbarger, et al., "Dental Cements", 5(4) Intl. Dental J. (1955), pp. 484-495.

Molander et al., "Microbiological root canal sampling: diffusion of a technology", 29 Intl. Endodontic J. (1996), pp. 163-167.

Ford, T.R., "The effects on the periapical tissues of bacterial contamination of the filled root canal", 15 Intl. Endodontic J. (1982), pp. 16-22.

Cook et al., "Effect of Trace Elements on Acid and Plaque Formation", Issue A, J. of Dental Res. (1975), p. 74.

Worner, H., "The Physical and Mechanical Properties of "Copper" Cements", 45(1) Austr. J. of Dentistry (1941), pp. 1-7.

* cited by examiner

*Primary Examiner*—Yvonne L Eyler
*Assistant Examiner*—Christopher R Lea
(74) *Attorney, Agent, or Firm*—Carl M. Nielsen

(57) ABSTRACT

Formulations and blends are described comprising zinc, silver, bismuth and copper in non-toxic amounts that are useful as treatments of a wide variety of conditions and diseases promoted by bacteria or other microorganisms.

6 Claims, No Drawings

ANTIMICROBIAL FORMULATIONS AND METHODS OF USING THE SAME

CROSS-REFERENCE TO RELATED APPLICATION

This application claims priority under Title 35 United States Code, § 119 to U.S. provisional patent application U.S. Pat. App. Ser. No. 60/542,636, filed Feb. 18, 2004.

FIELD OF INVENTION

The present invention relates to antimicrobial formulations and methods of using the same, and more particularly, the present invention relates to compositions useful to treat bacteria related conditions and diseases.

BACKGROUND OF THE INVENTION

Copper containing dental cements have been shown to demonstrate germicidal activity. See e.g., M. Dumas and M. Blush. *Bacteriocidal Effects of Copper Cements: A Review of the Literature*, Tufts Dental Outlook, 27 (2): 1-5 (1954). Similarly, silver has also been shown to have antimicrobial properties. See e.g., Hill et al., *Relative Efficiency of Germicidal Cements*, The Journal of the American Dental Association, 21 (3): 1565-1571 (1934).

Biofilms are diverse microbial colonies of bacteria, spirochetes, fungi, cocci, viruses, etc. that colonize and begin producing slime (mucopolysaccharides) that makes them invisible to the human immune system. Biofilms are resistant to immune cells and antibiotics. Microorganisms in a biofilm survive better and exhibit stronger resistance to the environment than do cells that are not in a biofilm. See e.g, Merritt et al., *Bacterial Biofilm and Dentistry*, CDA Journal, 29 (5): 355-360 (2001)). Biofilms are the chief contributors of dental disease. Biofilms can form in various environments, including within the mouth and in water supply lines Id.

Microorganisms are responsible for a number of diseases and adverse conditions in mammals. Moreover, while known to be effective against microbial related diseases and conditions, copper at high concentrations is generally toxic and causes discoloration of the teeth. Hence, there is a need for antimicrobial formulations that are non-toxic and effective against a wide variety of organisms and related diseases and conditions.

BRIEF SUMMARY OF THE INVENTION

The present invention is an antimicrobial formulation comprising a zinc compound such as zinc oxide from between about 2 to 90 percent by weight, a silver compound, from between about 005 to 2 percent by weight, a copper compound from between about 0.05 to 10 percent by weight and bismuth between about 2 to 50 percent by weight. The subject invention also includes an antimicrobial blend comprising the antimicrobial formulation plus a medium. The medium may be phosphoric acid and water and/or combinations thereof. The formulation of the subject invention may also be used in combination with a wide variety of cosmetic and pharmaceutical compositions including skin cream, petroleum jelly, astringent, composite resin, varnish, rose oil, nail polishes, ointments and bonding resins.

The present invention also provides for a novel process for preparing the antimicrobial formulation and methods of using the antimicrobial formulation to treat a variety of indications or conditions such as biofilms, skin irritation, and fungal infection.

DETAILED DESCRIPTION OF THE INVENTION

The present invention provides for formulations containing low non-toxic amounts of copper, silver, zinc and bismuth that are effective in treating microorganisms found in biofilm and other related diseases and conditions. For dental indications, the formulations of the present invention retard biofilm formation, eliminates existing biofilm and promotes secondary dentin formation. In other applications, indications, diseases or conditions, the formulations of the present invention retard microbial growth and treat irritated tissue. Specifically, the antimicrobial formulation can treat the growth of microorganisms on toenails, fingernails and hooves, and skin irritations. Also, the antimicrobial formulation can be used to treat the contamination of water lines. Specifically, the water lines of a dental unit.

The present invention provides formulations and blends that are highly antimicrobial, non-toxic, biocompatible, non-irritating to dental tissues, are color-fast, easy to prepare, have adequate setting time, have superior mechanical properties, promote secondary dentin formation and add years of longevity to fillings, castings and endodontic posts.

The formulations of the present invention are useful in combination with a wide variety of dental compositions and treatments including, but not limited to, resins, fillings, bases, periodontal packs, cements, sealers such as root canal sealers or root crack sealers and calcium hydroxide preparations for direct pulp caps.

The antimicrobial formulation of the subject invention may be provided in a powder or solid form. The formulation may be combined with a medium such as phosphoric acid or water to produce a blend. When the antimicrobial formulation is mixed with phosphoric acid, a zinc phosphate cement is made. The formulation may also be mixed with other compositions and substances described herein and/or used in combination with other compositions and substances.

The antimicrobial formulation of the present invention comprises a zinc compound such as zinc oxide from between about 2 to 90 percent by weight, a silver compound, from between about 0.05 to 2 percent by weight, a copper compound from between about 0.05 to 10 percent by weight and bismuth between about 2 to 50 percent by weight. Suitable zinc compounds for use in connection with the present invention include zinc oxide. Silver compounds useful in connection with the subject invention include silver chloride, silver phosphate and silver nitrate. Copper compounds useful in connection with the subject invention include cupric oxide, cuprous oxide, cuprous iodide, cupric iodide, cupric phosphate, copper (II) hydrogen phosphate, and cupric silicate.

The antimicrobial formulation of the subject invention may include other compounds. For example, iron or iron compounds may be added to further enhance the antimicrobial effect of the subject formulation. The antimicrobial formulations and blends of the subject invention may also be mixed with other compositions or used in combination with other compounds or dental compositions. For example, the formulation of the subject invention may be mixed with calcium hydroxide and placed on a tooth to protect against or retard decay. The formulation can also be combined with a composite resin and placed as a base. Also, if a medium such as phosphoric acid is added to the formulation, activated copper ions in the zinc phosphate cement leach into the dentin tubules and further assist in long term protection against decay and biofilm formation. The formulation of the present invention may also be used in combination with fluoride compounds including but not limited to sodium fluoride, and stannous fluoride.

The formulations and blends of the subject invention have low non-toxic concentrations of copper and are effective against biofilm formation as well as treating existing biofilm. The activated copper ions also protect teeth against decay, dental caries and plaque formation. Hence, the formulation of the subject invention is useful to treat tooth decay alone or in combination with other compounds such as stannous fluoride and sodium fluoride.

Copper is an important constituent of bone, bland, and nerve tissue and regulates the essential balance between all catabolic and anabolic processes of tissue metabolism. It is a cofactor in many enzymes necessary for connective tissue and bone formation, and protects the cells from oxidation as well as destructive affects of toxic agents from both external and internal sources. While the presence of iron facilitates the activity of copper in vital immune functions, copper is indispensable for the synthesis of heme in the heme factor of basal immunity, and is the prime factor in accelerating the synthesis of catalase, an antimicrobial enzyme. Disturbances in copper metabolism create nutritive imbalances in the metabolism of bone tissue, and contribute to build up of toxic effete material, decreased resistance, low immunity, low white blood cell count, degeneration of tissues, and malignancy. These deficiencies also reduce the life of the red blood corpuscles and the capacity of the bone marrow to produce them. In dental indications, copper increases local and general immunity and prohibits chronic inflammation and infection in tissues associated with local dental procedures. Copper supports tissue metabolism and enhancing detoxification of the oral cavity including the teeth and bone tissues.

Iron is another essential component in heme-factor immunity and is also found in the oxidation enzymes (cytochromes) of living tissues as well as in the enzyme myeloperoxidase that is essential for the production of white blood cells. It is also a component of catalase, an intracellular enzyme that destroys toxic byproducts of other metabolic processes and inflammations, as well as being an affective antidote against mineral and heavy metal toxins. Iron is an essential substance for the synthesis of enzymes and immune substances that destroy microorganisms. Disturbances in metabolism of iron result in degenerative processes, chronic infection and inflammation, and low general immunity. In dental indications, iron increases immune response and is a primary substance in helping to prevent chronic infection and pain in teeth and gums.

The formulations and blends of the present invention may be applied to a tooth without the need for the removal of all decayed tissue or exposure of the pulpal tissue. The present invention may be used to promote secondary dentin formation.

To facilitate the understanding of the invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

A "biofilm" is a colony of microorganisms attached to a solid surface. A biofilm colony can include bacteria, spirochetes, fungi, cocci, yeasts, protozoa, and other microorganisms. A "biofilm" includes the slime, mucopolysaccharides and other compounds produced by the microorganisms of a colony.

"Calcination" is the conversion of a metal into its oxide as a result of heating the metal to a high temperature.

"Dentin" is the calcified tissue surrounding the pulp cavity of a tooth.

"Activated" copper is copper which is missing one or more electrons.

In the formulation of the present invention, the antimicrobial effect of copper is increased when it is activated by silver. Silver activates copper galvanically as silver is a dissimilar metal to copper. Our ionic spin created by the activation of the copper allows the copper ions to penetrate biofilms and to retard microbial growth. This allows antimicrobial activity to be obtained without use of high concentrations of copper or silver.

It has been reported that copper ions may be activated by iron. Moreover, activated copper ions have been shown to be useful in certain dental compositions. Bismuth has been used shown to be effective in dental compositions containing copper ions. See e.g, M. Dumas and M. Blush. *Bacteriocidal Effects of Copper Cements: A Review of the Literature*, Tufts Dental Outlook, 27 (2): 1-5 (1954).

The present formulations may be used in combination with cosmetic and/or pharmaceutical compositions and related compounds such as alkyleneglycols, or alkyleneglycols in combination with one or more derivatives of hydroxyalkylcellulose, alcohols such as ethanol or propanol, glycols such as butylenes or hexylene glycol, polyols such as sorbitol or glycerol, polyethylene or polypropylene glycols. Biologically acceptable hydroxyalkylcelluloses may also be used in combination with the formulation of the present invention.

Topical treatments include use of the antimicrobial blend of the subject invention alone or in combination with a tissue compatible vehicle, such as a lotion-, ointment-, cream- or gel-based vehicle. Such vehicles are well known in the art and commercially available for formulation of active ingredients into a suitable form for topical application.

EXAMPLES

Example 1

Antimicrobial Useful as a Treatment for Skin Conditions and Disorders

|  | Percentage by weight |
| --- | --- |
| silica | 4 |
| magnesium oxide | 6 |
| zinc oxide | 81 |
| bismuth subnitrate | 5 |
| cuprous oxide | 2 |
| silver chloride | 1 |
| titanium oxide | 1 |

Silica, magnesium, zinc oxide and bismuth sub nitrate are first calcined (cinered, calcinated) by mixing the dry powders in sealed mixer. Then, the powder is placed in an airtight porcelain crucible and heated to 1,050° C. for three hours. The result is a fine powder, more medicinal and less toxic than an uncalcined powder of the same.

Next, the silver chloride is ground in a low oxygen, low light environment to protect the compound. The silver chloride powder is then mixed uniformly together with the calcined powder in the sealed mixer.

Cuprous iodide is then added to the mixture and thoroughly mixed in the sealed container: then, titanium oxide is gradually mixed into the formula-starting at 0.25% by weight to a maximum of 1% by weight, until the desired shade is achieved. White copper cement is in its untreated state, yellowish. Titanium oxide will at 1% make the powder snow white. Different individual preferences for color may thus be accommodated.

This formulation may be used as a powder or mixed with an aqueous or non-aqueous medium and/or in combination with vaseline jelly and the like.

Example 2

Antimicrobial Formulation Useful as a White Copper Cement

|  | Percentage by weight |
| --- | --- |
| silica | 4 |
| magnesium oxide | 6 |
| zinc oxide | 81 |
| bismuth subnitrate | 5 |
| cuprous oxide | 2 |
| silver chloride | 1 |
| titanium oxide | 1 |

This formulation is antimicrobial, highly biocompatible, color fast, easy to mix, has adequate setting time; easy to clean after setting, adds years of longevity to fillings, castings and endodontic posts and promotes secondary dentin formation.

This formulation may be used as a powder or mixed with an aqueous or non-aqueous medium.

As discussed above, the formulation may be heated at high temperatures for a prolonged period of time in order to calcinate the white copper cement.

Example 3

Antimicrobial Formulation Useful for Preparing Red Copper Cement

|  | Percentage by weight |
| --- | --- |
| silica | 4 |
| magnesium oxide | 6 |
| zinc oxide | 73 |
| bismuth subnitrate | 5 |
| ferric oxide | 3 |
| cupric oxide | 7 |
| silver chloride | 1 |

Silica, magnesium, zinc oxide, bismuth sub nitrate and ferric oxide are first calcined (cinered) by mixing the dry powders in a sealed mixer. The mixture is then placed in an airtight porcelain crucible and heated to 1,050° C. for three hours. The result is a fine powder said to be more medicinal and less toxic than an uncalcined equivalent.

The silver chloride is then made finer by grinding or crushing in a low oxygen, low light environment to protect the compound from oxidation and color change. Following this procedure the silver chloride powder is mixed uniformly along with the above calcined base in the sealed mixer. The cupric oxide may be added at the same point and thoroughly mixed, leaving a red powder which completes the formulation.

This formulation is antimicrobial, highly biocompatible, color fast, easy to mix, has adequate setting time, easy to clean after setting, adds years of longevity to fillings, castings and endodontic posts and promotes secondary dentin formation. Red copper cement can directly impact and reduce tendencies to the pathological patterns and tissues on a bio-energetic functions level including follicular cysts, dental fistula, dental foot granuloma, fundus abscess, gingival sulcus, ulcerous gingivitis, maxillary ostitis, exudative ostitis, sclerotic ostitis, pepto-streptococci, *borrelia burgdorfer*, gangrenous pulpa, acute pulpitis, and caries.

This formulation may be used as a powder or mixed with an aqueous or non-aqueous medium. This formulation may be heated at high temperatures for a prolonged period of time in order to calcinate the formulation used to make red copper cement. The formulation of Example 3 is particularly useful in preventing and treating dental decay alone or in combination with fluoride compounds such as stanneous fluoride and sodium fluoride between about 0.05 weight percent and 5 weight percent.

Also, the red copper powder of Example 3 may be mixed with a combination of 400 ppm ethyl ether anhydrous and/or COPALITE WE® (a dental varnish without chloroform) to treat fungal toenails. To date, this composition has been successful in nine instances in treating fungal toenails that were resistant to over the counter and prescription medications.

Example 4

Root Canal Sealer

|  | Percentage by weight |
| --- | --- |
| zinc oxide | 4 |
| partially hydrogenated rosin | 25 |
| bismuth subcarbonate | 14 |
| barium sulfate | 11 |
| sodium borate | 2 |
| cuprous oxide | 7 |
| silver chloride | 1 |

This formulation may be mixed in with combination of 400 ppm ethyl ether anhydrous and/or Copalite WE® (a dental varnish without chloroform) and may be used to seal root canals when eugenol liquid is the medium.

Example 5

Treating Fungal Toenails and Fingernails

|  | Minimum % by weight | Maximum % by weight |
| --- | --- | --- |
| Silver nitrate | 0.05 | 2 |
| Cuprous oxide or cupric oxide | 2 | 10 |
| Bismuth Subnitrate | 2 | 50 |
| Zinc Oxide | 2 | 90 |
| Magnesium Oxide | 2 | 10 |
| *Echinacea* | 0.25 | 5 |
| Antimony | 0.05 | 1 |
| *Belladonna* | 0.05 | 0.5 |

Rose oil is added as an emulsifier in an amount from 1 to 100 grams

The formulation may be used as a powder or mixed with an aqueous or non-aqueous medium. For example, the formulation may be mixed with an astringent.

The antimicrobial formulation is then applied directly to the afflicted area as needed.

Example 6

Treating Skin Irritation

|  | Minimum % by weight | Maximum % by weight |
|---|---|---|
| Silver nitrate | 0.05 | 2 |
| Cuprous oxide or cupric oxide | 2 | 10 |
| Bismuth | 2 | 50 |
| Zinc | 2 | 90 |
| Magnesium | 2 | 10 |
| *Echinacea* | 0.25 | 5 |
| Antimony | 0.05 | 1 |
| *Belladonna* | 0.05 | 0.5 |

Rose oil is added as an emulsifier in an amount from 1 to 100 grams.

The formulation may be used as a powder or mixed with an aqueous medium or other composition or substance. For example, the formulation may be mixed with petroleum jelly.

The antimicrobial formulation is then applied directly to the afflicted area as needed.

Example 7

Treating White Line Disease in Horses

|  | Percentage by weight |
|---|---|
| silica | 4 |
| magnesium oxide | 6 |
| zinc oxide | 81 |
| bismuth subnitrate | 5 |
| cuprous oxide | 2 |
| silver chloride | 1 |
| titanium oxide | 1 |

White Line Disease in horses is a deterioration of the inner portion of the hoof wall and occurs at the hoof wall/sole junction. The separation at the hoof wall/sole junction allows microorganisms to enter.

The formulation may be used as a powder or mixed with an aqueous or non-aqueous medium or other composition or substance.

The antimicrobial formulation is applied directly to the afflicted area as needed.

Example 8

Treating Dental Water Lines

|  | Percentage by weight |
|---|---|
| silica | 4 |
| magnesium oxide | 6 |
| zinc oxide | 81 |
| bismuth subnitrate | 5 |
| cuprous oxide | 2 |
| silver chloride | 1 |
| titanium oxide | 1 |

The formulation may be used as a powder or mixed with an aqueous medium.

The formulation is introduced into the water lines of a dental unit and the liquid is allowed to remain undisturbed overnight. The next morning, the lines are rinsed for one minute. Commercial test kits indicate that the water lines of the dental unit were purged of microbes.

Example 9

Efficacy of Dental Cement in Biofilm Prevention in a Stagnant System

Three types of standard sized coupons with a fine grained antimicrobial containing powder of the dental cement were used (labeled 1, 2 and 3). The tests were performed in stagnant test tubes.

Three types of dental cement coupons (labeled 1, 2 and 3), dental cement powder and polycarbonate coupons (as an untreated control) were place into test tubes with 5 mL sterile tryptic soy media at a concentration of 30 mg/L. Each type of coupon was placed into 3 separate test tubes (for 3 replicates). The dental cement powder was placed in the test tube a concentration of 1 g/L (5 mg/5 mL). Each of the test tubes was capped to insure sterility was maintained and allowed to sit for 48 hours to facilitates dissolution of the biocide from the coated coupons. Following this, each of the test tubes received a 100 μL bolus containing *Staphylococcus aureus* at a concentration of $2.8 \times 10^3$ cells. A single control tube for each coupon type (and powder) received no inoculum. Prior to inoculation, *S. aureus* was grown from frozen stock culture in TSB media to the necessary concentration. Following inoculation, tubes were covered and incubated for 48 hours, after which the coupon was removed and attached biofilm was physically scraped into dilution buffer, disaggregated using a tissue homogenizer and serially diluted and plate on R2A agar. Results are reported as $CFU/cm^2$ on the coupon surface.

While uncoated polycarbonate coupons exposed to the *S. aureus* inoculum indicated cell colonization at an average density of $1.08 \times 10^6$ $CFU/cm^2$, none of the dental cement coupons contained any measurable biofilm accumulation (Table 1). All dental cement formulations tested, and the dental cement powder, were 100% effective in preventing biofilm accumulation under the condition tested.

TABLE 1

| Coupon | $CFU/cm^2$ |
|---|---|
| Dental cement #1A (inoculated) | 0 |
| Dental cement #1B (uninoculated) | 0 |
| Dental cement #1C (inoculated) | 0 |
| Dental cement #2A (uninoculated) | 0 |
| Dental cement #2B (inoculated) | 0 |
| Dental cement #2C (inoculated) | 0 |
| Dental cement #3A (inoculated) | 0 |
| Dental cement #3B (inoculated) | 0 |
| Dental cement #3C (uninoculated) | 0 |

TABLE 1-continued

| Coupon | CFU/cm$^2$ |
|---|---|
| Dental cement #4A (uninoculated) | 0 |
| Dental cement #4B (inoculated) | 0 |
| Dental cement #4C (inoculated) | 0 |
| Polycarbonate #5A (uninoculated) | 0 |
| Polycarbonate #5B (inoculated) | 5.00E + 05 |

Example 10

Reactivity Testing and Biological Resonance Testing

The disclosed formulations have been shown by reactivity testing for IgG, IgM and IgA antibody production to be biocompatibility superior to other zinc phosphate cements. Furthermore, biological resonance testing has shown that the disclosed formulations are less susceptible to the following pathological disorders and/or disease-causing organisms: follicular cysts, dental fistula, dental root granuloma, fundus abscess, gingival sulcus, ulcerous gingivitis, maxillary ostitis, exudative ostitis, sclerotic ostitis, gangrenous pulpa, acute pulpitis, caries, pepto-streptococci and caries.

Example 11

Efficacy of Dental Cement to Prevent Biofilm in a Stagnant System

The efficacy of the dental cement of the subject invention has been tested in "stagnant" test tubes and shown to be effective in preventing biofilm formation.

A growth curve study of Streptococcus mutans ATCC 25175 and Lactobacills paracasei was completed in order to determine optimal media concentration and time necessary for the organisms to reach log phase. S. mutans was grown anaerobically in full-strength Brain Heart Infusion (BHI) broth and L. paracasei was grown aerobically in full strength Lactobacilli MRS broth. Both cultures were incubated at 37° C. Based on the growth curve study, it was determined that S. mutans reaches log phase after 22 hours of anaerobic incubation in BHI broth at 37° C. L. paracasei reach log phase after 46 hours of aerobic incubation Lactobacilli MRS broth at 37° C.

Eight coupons of each type were placed in glass scintillation vials and autoclaved. Sterile BHI broth at a concentration of 37 mg/L and sterile Lactobacilli MRS broth at a concentration of 55 mg/L was added to appropriate vials. The tubes were incubated at room temperature for 48 hours. The tubes were inoculated with 100 µl of S. mutans or L. paracasei grown for the appropriate amount of time at a concentration 10$^3$-10$^4$ CFU/ml. Vials inoculated with S. mutans were incubated anaerobically for 48 hours at room temperature. Vials inoculated with L. paracasei were incubated for 48 hours aerobically at room temperature.

At the end of the 48 hour incubation, the coupons were removed from the vials, scraped to remove biofilm. The biofilm samples were disaggregated via homogenization. The samples were diluted and plated on tryptic soy agar. S. mutans samples were incubated anaerobically for 60 hours at 37° C. L. paracasei samples were incubated aerobically for 60 hours at 37° C.

The results of this testing are provided in Table 2 immediately below.

TABLE 2

Test Tube Designation, Inoculum, Media and Average Colonization.

| Tube Numbers | Coupon Type | Innoculum | Media | Average Colonization (CFU/cm$^2$) |
|---|---|---|---|---|
| 1-3 | GLS | S. mutans | BHI | 0 |
| 4-6 | GLS | Lactobacillus | MRS | 684 |
| 7 | GLS | none | BHI | 0 |
| 8 | GLS | none | MRS | 0 |
| 9-11 | RCC | S. mutans | BHI | 0 |
| 12-14 | RCC | Lactobacillus | MRS | 0 |
| 15 | RCC | none | BHI | 0 |
| 16 | RCC | none | MRS | 0 |
| 17-19 | WC | S. mutans | BHI | 0 |
| 20-22 | WC | Lactobacillus | MRS | 0 |
| 23 | WC | none | BHI | 0 |
| 24 | WC | none | MRS | 0 |
| 25-27 | WC+ | S. mutans | BHI | 0 |
| 28-30 | WC+ | Lactobacillus | MRS | 0 |
| 31 | WC+ | none | BHI | 0 |
| 32 | WC+ | none | MRS | 0 |
| 33-35 | PC | S. mutans | BHI | 0 |
| 36-38 | PC | Lactobacillus | MRS | 210 |
| 39 | PC | none | BHI | 0 |
| 40 | PC | none | MRS | 0 |

Cement Coupons:

GLS=Fuji II Glass Ionomer Cement Lot#75 N05K K by GC America

RCC=DOC'S BEST Red Copper Zinc Phosphate Cement (Lot# A2920-9)

WC=DOC'S BEST White Copper Zinc Phosphate Cement (Lot#i3810-6)

WC+=White Copper of Example 2

PC=Durelon Cement Lot#166317 by 3M

RCC is made from a formulation of the following compounds in the approximate amounts by weight percent: zinc oxide (75-85); magnesium oxide (7-8.5); cupric oxide (5.5-6.5); bismuth subnitrate (2.5-3.5); silica (1.5-2.5); iron oxide (less than 1.5); and sodium fluoride (less than 0.1) and mixed with phosphoric acid medium.

WC is made from a formulation of the following in the approximate amounts by weight percent: zinc oxide (75-85); magnesium oxide (7-8.5); cuprous oxide (6.5-7.5); bismuth subnitrate (2.5-3.5); silica (1.5-2.5); and sodium fluoride (less than 0.1) and mixed with a phosphoric acid medium.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed is:

1. A formulation comprising:
(a) about 4% by weight silica;
(b) about 6% by weight magnesium oxide;
(c) about 73% by weight zinc oxide;
(d) about 5% by weight bismuth subnitrate;
(e) about 3% by weight ferric oxide;
(f) about 7% by weight cupric oxide; and
(g) about 1% by weight silver chloride.

2. A formulation comprising:
(a) about 4% by weight silica;
(b) about 6% by weight magnesium oxide;
(c) about 81% by weight zinc oxide;
(d) about 5% by weight bismuth subnitrate;
(e) about 2% by weight cupric oxide;
(f) about 1% by weight silver chloride; and
(g) about 1% by weight titanium chloride.

3. A formulation comprising:
(a) about 4% by weight zinc oxide;
(b) about 25% by weight staybelite resin;
(c) about 14% by weight bismuth subcarbonate;
(d) about 11% by weight barium sulfate;
(e) about 2% by weight sodium borate;
(f) about 7% by weight cuprous oxide; and
(g) about 1% by weight silver chloride.

4. A kit comprising: (1) an antimicrobial formulation comprising: (a) about 4% by weight silica;(b) about 6% by weight magnesium oxide; (c) about 73% by weight zinc oxide; (d) about 5% by weight bismuth subnitrate; (e) about 3% by weight ferric oxide; (f) about 7% by weight cupric oxide; and (g) about 1% by weight silver chloride; and (2) phosphoric acid, a dental varnish, stannous fluoride or sodium fluoride.

5. A kit comprising: (1) an antimicrobial formulation comprising: (a) about 4% by weight silica; (b) about 6% by weight magnesium oxide; (c) about 81% by weight zinc oxide; (d) about 5% by weight bismuth subnitrate; (e) about 2% by weight cupric oxide; (t) about 1% by weight silver chloride; and (g) about 1% by weight titanium chloride; and (2) phosphoric acid, a dental varnish, stannous fluoride or sodium fluoride.

6. A kit comprising: (1) an antimicrobial formulation comprising: (a) about 4% by weight zinc oxide; (b) about 25% by weight staybelite resin; (c) about 14% by weight bismuth subcarbonate; (d) about 11% by weight barium sulfate; (e) about 2% by weight sodium borate;(f) about 7% by weight cuprous oxide; and (g) about 1% by weight silver chloride; and (2) phosphoric acid, a dental varnish, stannous fluoride or sodium fluoride.

* * * * *